US006916967B2

United States Patent
Wright et al.

(10) Patent No.: US 6,916,967 B2
(45) Date of Patent: Jul. 12, 2005

(54) ADHESIVE BANDAGE FOR PROTECTION OF SKIN SURFACES

(75) Inventors: Gregory Wright, Wilmington, MA (US); Mark Waltzman, Newton, MA (US)

(73) Assignee: Venture Tape Corp., Rockland, MA (US)

( * ) Notice: Subject to any disclaimer, the term of this patent is extended or adjusted under 35 U.S.C. 154(b) by 14 days.

(21) Appl. No.: 10/616,443

(22) Filed: Jul. 9, 2003

(65) Prior Publication Data

US 2005/0010154 A1 Jan. 13, 2005

(51) Int. Cl.[7] .............................................. A61F 13/00
(52) U.S. Cl. ........................... 602/42; 602/43; 602/54; 128/888; 128/889
(58) Field of Search .............................. 602/41–43, 57, 602/54; 128/888, 889

(56) References Cited

U.S. PATENT DOCUMENTS

| | | | |
|---|---|---|---|
| 2,992,644 A | 7/1961 | Plantinga et al. | |
| 3,416,525 A | 12/1968 | Yeremian | |
| 3,927,669 A | 12/1975 | Glatt | |
| 4,126,130 A | 11/1978 | Cowden et al. | |
| 4,561,435 A | 12/1985 | McKnight et al. | |
| 4,616,644 A | 10/1986 | Saferstein et al. | |
| 4,671,266 A | 6/1987 | Lengyel et al. | |
| 4,901,714 A | 2/1990 | Jensen | |
| 5,170,781 A | 12/1992 | Loomis | |
| 5,336,209 A | 8/1994 | Porzilli | |
| 5,512,041 A * | 4/1996 | Bogart | 602/58 |
| 5,954,679 A | 9/1999 | Baranitsky | |
| 6,343,604 B1 | 2/2002 | Beall | |
| 6,362,387 B1 * | 3/2002 | Carlson et al. | 602/41 |
| 6,384,294 B1 | 5/2002 | Levin | |
| 2002/0128580 A1 | 9/2002 | Carlson et al. | |

* cited by examiner

*Primary Examiner*—Kim M. Lewis
(74) *Attorney, Agent, or Firm*—Wolf, Greenfield & Sacks, P.C.

(57) ABSTRACT

An adhesive bandage is disclosed for protecting blisters or wounds, or for preventing chaffing or the formation of blisters. In one embodiment, the bandage includes a protective layer for covering the blister or area of skin to be protected, and an adhesive layer surrounding the protective layer. The opposite side of the bandage contains a low-friction layer or surface and a separate sheet of low-friction material adjacent to but movable with respect to the low-friction layer or surface. The sheet of low-friction material is attached to the bandage in such a way that it can move with respect to the bandage in response to frictional forces, thereby minimizing a transfer of frictional forces from clothing or the like to the bandage. A method of treating blisters, as well as a method of preventing chaffing and the formation of blisters are also disclosed.

27 Claims, 3 Drawing Sheets

ADHESIVE BANDAGE FOR PROTECTION OF SKIN SURFACES

FIELD OF THE INVENTION

This invention relates generally to bandages, and more particularly to adhesive bandages for protecting skin from frictional forces.

BACKGROUND

Blistering of the skin typically is caused by some type of trauma. One example of such trauma is friction between an item of clothing or a shoe, and the skin surface beneath the clothing or shoe. Another example of such trauma is scalding or burning of the skin by a heated or cold object or fluid. Blisters may form as a result of, for example, a second-degree burn caused by scalding water or gas, or contact with a hot surface. Another example of trauma is an infection or disease such as pemphigus. Such trauma causes fluid to collect in a blister structure either under the epidermis or within the epidermis. This fluid is sterile, and protects the underlying dermal layer from pathogens. Preferably, the blister structure should be prevented from popping until healing has occurred to maintain protection of the underlying dermal layer. Once healing has occurred, the fluid within the blister is reabsorbed into the body, and the overlying, dead tissue may either fall away or, if necessary, be debrided. Regardless of the cause of the blister, a blister may be popped as a result of frictional forces that bear on the blister, puncture from a sharp instrument or the application of pressure to the blister.

Typically, blisters or wounds are covered with bandages or the like to prevent direct frictional contact between clothing or other surfaces and the blister or wound, or to prevent sharp instruments from puncturing the blister. Such conventional bandages generally include a sterilized pad centrally mounted on a relatively larger adhesive strip such that the adhesive strip extends past the sterilized pad on either side, or all around the perimeter thereof. When the sterilized pad is placed over a blister, the extended portion of the adhesive strip adheres to the skin adjacent to the blister to maintain the pad in place. However, with many such conventional bandages, friction applied to the bandage by clothing or the like may be transferred to the surface of the blister, causing it to pop or to a wound, causing further damage to the wound.

Chaffing of the skin also may be caused by rubbing of clothing or footwear against the skin. Chaffing is a particular concern for runners, such as chaffing caused by clothing rubbing against the nipples which produces much discomfort.

Chaffing and blisters that result from frictional interaction between clothing or footwear and the skin may be prevented if such friction is reduced or prevented. Bandages have been proposed to prevent chaffing and the formation of blisters or other damage to the skin caused by such frictional forces. Conventional bandages used for this purpose typically are ineffectual, for the reasons discussed above, since the bandage itself will be caused to rub against the skin by the clothing or the footwear, and this rubbing also can cause blisters or other damage.

The ineffectiveness of conventional bandages for preventing chaffing, blisters or other injury or for protecting wounds or blisters is particularly acute with respect to blisters caused by ill-fitting footwear in which a portion of the footwear repeatedly rubs against the skin. This repeated rubbing produces and maintains the blister each time the footwear is worn. Such rubbing forces imposed on bandages, whether compressive or shear forces, often are transmitted to the inner protective layer of the bandage and to the underlying skin. Those forces either injure the area or, if it is injured already, prevent the area from properly healing.

Although bandages for preventing chaffing, protecting blisters and absorbing forces are known, there is a need for improved structures that are more effective in shielding an injured area of the skin and preventing injury. Examples of known bandages are disclosed in the following U.S. patents and published application: U.S. Pat. Nos. 2,992,644; 3,416,525; 3,927,669; 4,126,130; 4,561,435; 4,616,644; 4,671,266; 4,901,714; 5,170,781; 5,336,209; 5,954,679; 6,343,604; 6,384,294; and 2002/0128580.

SUMMARY OF INVENTION

In one aspect, this invention discloses an adhesive bandage which includes a substrate in which a second surface has a low-coefficient of friction, and in which a first surface includes a protective layer and a layer of a pressure-sensitive adhesive surrounding at least a portion of the protective layer, and a sheet of material which is attached to the substrate at attachment locations adjacent the perimeter of the substrate. The sheet of material has a lower surface with a low coefficient of friction, the lower surface of the sheet confronting the second surface of the substrate and being constructed and located to move with respect to the second surface of the substrate in a direction generally parallel to the substrate. In one embodiment of this aspect, the substrate is generally rectangular, and the sheet of material is attached to the substrate only at corners of the substrate. In yet another embodiment, the sheet of material includes cutouts between the attachment locations. In yet another embodiment of this aspect, the layer of adhesive extends to a point spaced from the perimeter of the substrate along certain edges to provide extensions of the substrate which are not covered by adhesive and are sufficiently flexible to permit greater movement of the sheet of material. In some embodiments, these extensions are disposed around the entire perimeter of the substrate, and in other embodiments, the extensions are disposed on opposite sides of the protective layer. In yet other embodiments, the sheet of material is attached all the way around the perimeter of the substrate either at spaced locations, or continuously.

In another aspect of the invention, a bandage is disclosed which includes a first layer having a first, low-friction surface, and a second surface on which an adhesive layer is disposed, the adhesive layer extending to an adhesive edge which is spaced inwardly of the outer perimeter of the first layer at selected locations, and a second layer of low-friction material disposed adjacent the first surface of the first layer, the second layer of low-friction material being attached to the first layer at selected locations spaced from the adhesive edge toward the outer perimeter of the first layer. In one embodiment of this aspect, the first and second layers are rectangular in shape, and the second layer is attached to the first layer substantially at corners thereof. In another embodiment, the second layer includes cutouts between the corners. In yet another embodiment, the second layer is affixed around its entire peripheral edge to the first layer. In another embodiment a protective layer is centrally disposed on the second surface of the first layer and surrounded by the layer of adhesive. In yet another embodiment, the first layer is heat-welded to the second layer. In yet another further embodiment, the second layer and the first layer are integrally formed as a single sheet, and the locations of attachment are formed as a crease in this sheet.

In yet another aspect of the invention, a bandage for the skin is disclosed which includes a first layer formed of a low-friction material having an upper and lower surface, a protective layer disposed on the lower surface of the first layer, a layer of adhesive surrounding the protective layer, and a second layer of a low-friction material adjacent the upper surface of the first layer such that the second layer moves with respect to the upper surface of the first layer in a direction generally parallel to the upper surface in response to forces applied to the second layer. In one embodiment of this aspect, the second layer is only attached to the upper surface of the first layer at selected locations, such as at corners thereof. In another embodiment, the adhesive layer on the lower surface of the first layer extends to an adhesive edge that is spaced from an outer edge of the first layer. In yet another embodiment, the second layer is attached to the first layer only at locations spaced from the adhesive edge toward the outer edge of the first layer.

In yet another aspect of this invention, a method for treating a blister is disclosed which includes placing a bandage over a blister so that the blister is covered by a protective layer, securing the bandage to the skin using a layer of a pressure sensitive adhesive that surrounds but does not touch the blister, and affixing a sheet of low-friction material adjacent another side of the bandage, the sheet of low-friction material being constructed to be positioned between the bandage and items of clothing and being movable with respect to the bandage to minimize transfer of any friction forces from the items of clothing to the blister.

In yet another aspect of the invention, a method for protecting an area of the skin from chaffing or from blistering is disclosed which includes placing a protective layer of a bandage against an area of skin that is to be protected, adhesively securing the bandage to the skin using a layer of pressure-sensitive adhesive that surrounds but does not touch the area of skin to be protected, placing a low-friction surface on the side of the bandage opposite the protective layer and adhering a layer of a low-friction material to the bandage between the low-friction surface of the bandage and items of clothing, the layer of low-friction material being movable with respect to the low-friction surface on the bandage to minimize the transfer of any friction forces from clothing to the area of skin to be protected.

BRIEF DESCRIPTION OF THE DRAWINGS

The objects, advantages and features of this invention will be more clearly appreciated from the following Detailed Description, when taken in conjunction with the accompanying drawings, in which.

DETAILED DESCRIPTION

In one aspect, the present invention relates to an adhesive bandage structure which serves both to protect existing wounds or blisters from damage caused by frictional forces, and to prevent blisters or wounds from forming due to the action of frictional forces on exposed skin. Such a bandage structure may be used with patients suffering from second-degree burns, such as those which result from scalding water or gas, or patients suffering from infection-related blisters, or simply patients having blisters or wounds resulting from friction on the skin such as those caused by shoes and the like. In addition, such a bandage structure may be used proactively to prevent the formation of blisters or wounds that are caused by friction forces acting on the skin.

In one embodiment, the bandage structure of the present invention includes a substrate or a layer or sheet of material which has a layer of gauze or other like protective material attached to one side. A layer of a pressure-sensitive adhesive is disposed on the same side of the substrate as the gauze pad, and either surrounds the gauze pad, or is disposed on both sides thereof. This pressure-sensitive adhesive is one that is suitable for affixation to the skin. Disposed on the other side of the substrate from the gauze pad and the adhesive layer is a layer or coating of a low-friction material. Alternatively, the entire substrate may be formed of this low-friction material. One example of such a low-friction material is a low-density polyethylene. Covering this layer or coating of low-friction material on the substrate is another sheet of low-friction material which is attached to the substrate and/or the coating or layer of low-friction material disposed on the substrate. The sheet of low-friction material is in direct contact with the coating or layer of low-friction material disposed on the other side of the substrate. The sheet of low-friction material is attached in such a manner that it may slide with respect to the substrate in a direction generally parallel to the low-friction layer or coating on the substrate. This attachment may be made in one of several ways. In one embodiment, the second sheet of material is attached to the substrate, or the low-friction coating or layer on the substrate at extensions that are disposed beyond the area covered by the adhesive layer. In another embodiment, the sheet of low-friction material is attached only at selected locations. For example, if it has a square configuration, the sheet of low-friction material is only affixed at its corners. Moreover, cutouts may be provided to permit additional movement.

Figure 1:
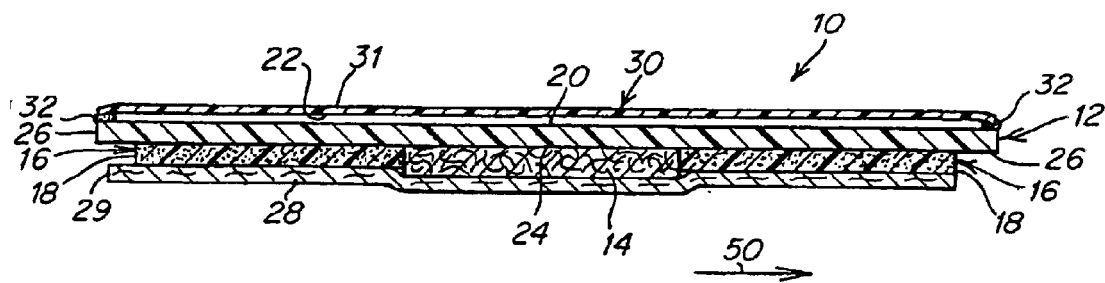
FIG. 1 is a cross-sectional view of one embodiment of the bandage of this invention.

With reference now to the drawings and more particularly to FIG. 1 thereof, one embodiment of a bandage structure 10 of this invention will be described. Structure 10 includes a first layer or substrate 12 having an upper surface 20 and a lower surface 24. Mounted onto the lower surface 24 of substrate 12 is a protective layer 14. Surrounding the protective layer 14 on at least on two sides thereof, is an adhesive layer 16 that is mounted on lower surface 24. Typically, although not necessarily, a release liner 28 or the like covers adhesive layer 16 as well as protective layer 14. Disposed adjacent and generally parallel to upper surface 20 is a sheet or layer 30 having an upper surface 31 and a lower surface 22.

Typically, upper surface 20 of substrate 12 is covered by a layer of or is formed of a low-friction material. Such a low-friction material may be formed as a coating on upper surface 20 or as a layer affixed to upper surface 20, or substrate 12 itself may be entirely formed of a low-friction material. If substrate 12 is made of some material other than a low-friction material, such as a flexible paper, metal foil or plastic material, it may be coated on surface 20 with a layer or coating of a low-friction material. Lower surface 22 of layer 30 is also formed of a low-friction material. Similar to substrate 12, lower surface 22 may be coated with a low-friction material, or it may be covered with a layer of low-friction material or layer 30 may itself be entirely formed of a low-friction material.

Layer 30 is connected to substrate 12 and/or upper surface 20 at connection locations 32. Locations 32 typically are along or adjacent a peripheral edge or perimeter of substrate 12 as well as along or adjacent a peripheral edge or perimeter of layer 30. In this way, layer 30 is permitted to readily move or slide with respect to substrate 12 in a direction generally parallel to surfaces 20 and 22, in the direction of arrow 50 in FIG. 1.

Protective layer 14 is of a conventional design and composition, and typically is a sterile pad which may be made of gauze or absorbent plastic or the like. Adhesive layer 16 is formed of a conventional, pressure-sensitive adhesive that will readily adhere to human skin, that is non-toxic and that can be removed from the skin without injuring the skin. Typical examples of a suitable adhesive for adhesive layer 16 are a tackified acrylic adhesive, a rubber adhesive, a latex adhesive, or a urethane adhesive. Release liner 28 is conventional, and typically includes a silicone-coated substrate permitting quick release or removal of liner 28 from adhesive layer 16 and may include a flap 29 to be grasped for removal. Typical examples of release liner 28 are a silicone coated paper strip, a paper strip encapsulated in a plastic extrusion and coated with silicone, and silicone coated strips formed of polyester, polyethylene or polypropylene.

The low-friction material forming surfaces 20 and 22 or disposed thereon typically has a low static coefficient of friction, and typically is supple and strong. Surfaces 20 and 22 preferably have a static coefficient of friction which is lower than that of a typical skin surface and of layer 14. In one embodiment, a preferred static coefficient of friction is less than 1.0. In another embodiment, the static coefficient of friction is less than about 0.7. In another embodiment, the static coefficient of friction is within the range of from about 0.05 to about 0.7. One example of a suitable material is a low-density polyethylene having a static coefficient of friction of about 0.2 or less. Other examples include standard polyethylene, polyester, polytetrafluoroethylene, expanded polytetrafluoroethylene, polypropylene and the like. As used herein, the terms "coefficient of friction" or "static coefficient of friction" shall mean the static coefficient of friction for plastic film and sheeting as determined according to ASTM D1894.

Layer 30 is attached to substrate 12 at locations 32 such that layer 30 is permitted to slide or move with respect to substrate 12 in a direction generally parallel to surfaces 20 and 22 upon the application of a force to the upper surface of layer 30. Typically, but not necessarily, the outer edge or perimeter of layer 30 is connected to the outer edge or perimeter of substrate 12. There are many different embodiments of the connections 32 and of the locations of connections 32 which would permit the desired sliding movement between layer 30 and substrate 12.

Figure 2:
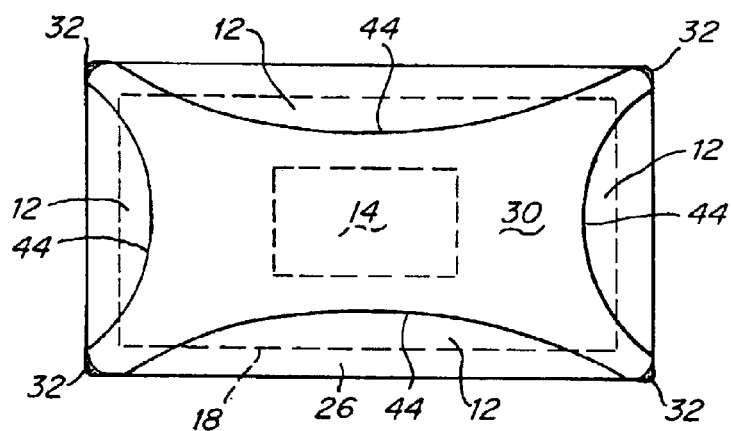
FIG. 2 is a top plan view of the bandage of FIG. 1.
Figure 3:
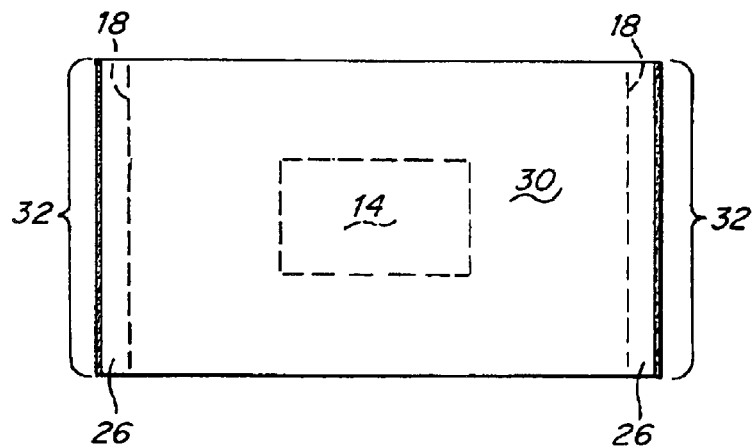
FIG. 3 is a top plan view of another embodiment of the bandage of this invention.
Figure 6:
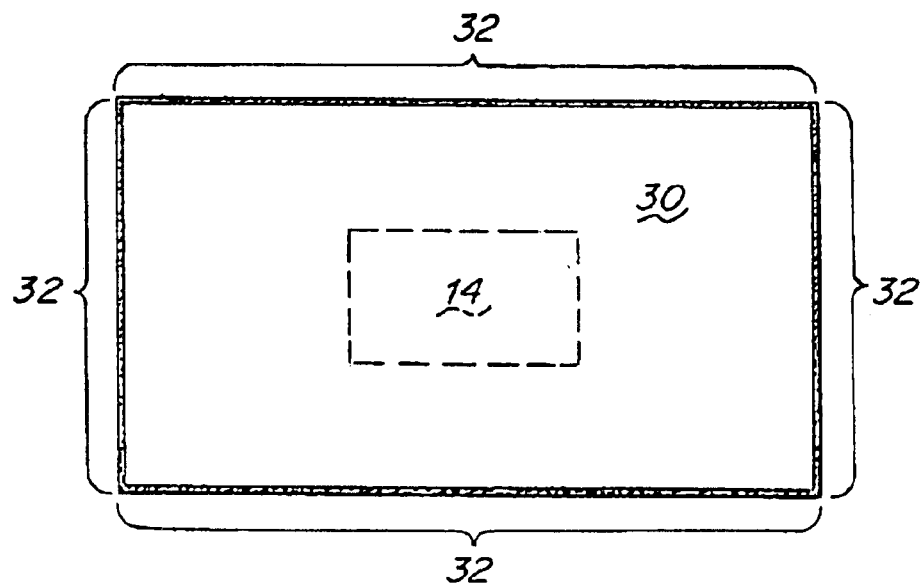
FIG. 6 is a top plan view of yet another further embodiment of the bandage of this invention.

The exact positioning of connections 32 depends on the shape of structure 10. Examples are shown in FIGS. 1, 2, 3 and 6 for a square or rectangular structure. In the example of FIGS. 1 and 2, there is a connection 32 at each corner of structure 10, or at each corner of the rectangle or square. In another embodiment, as illustrated in FIG. 3, layer 30 is connected to substrate 12 along two opposed edges of substrate 12 on opposite sides of protective layer 14. In another embodiment of a rectangular structure, layer 30 is connected to substrate 12 at its edge around the entire perimeter of substrate 12, as shown in FIG. 6.

Figure 4:
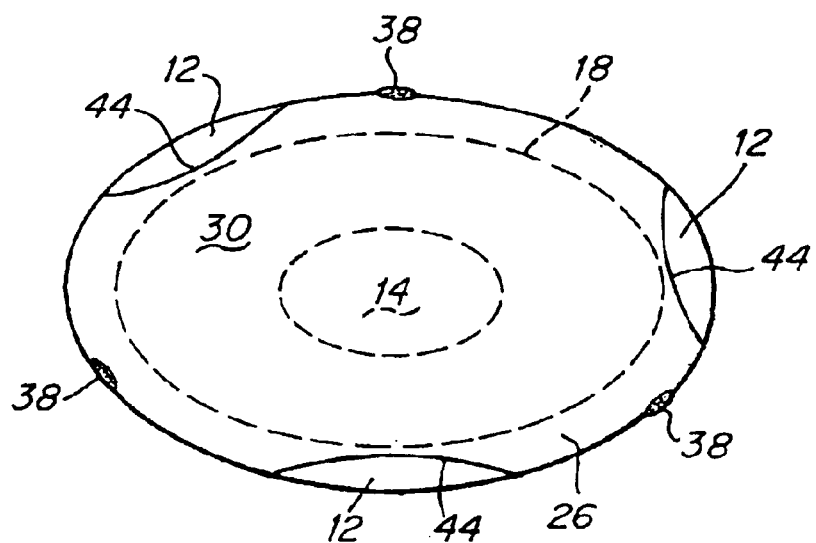
FIG. 4 is a top plan view of yet another embodiment of the bandage of this invention.
Figure 5:
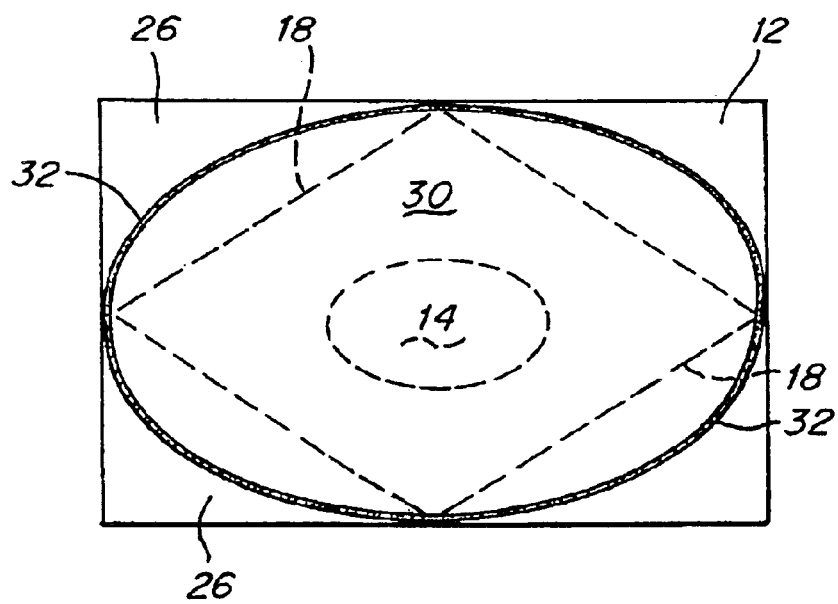
FIG. 5 is a top plan view of yet another further embodiment of the bandage of this invention.

In other embodiments, such as those shown in FIGS. 4 and 5, in which layer 30 has an oval or circular shape, layer 30 may be attached to substrate 12 at spot connections 38 around the oval edge of layer 30, as shown in FIG. 4, in which three connections 38 are illustrated. In FIG. 5, layer 30 is secured around its entire perimeter to substrate 12. It is noted that in FIG. 5, layer 30 is oval or circular in shape, while substrate 12 is rectangular in shape.

Figure 7:
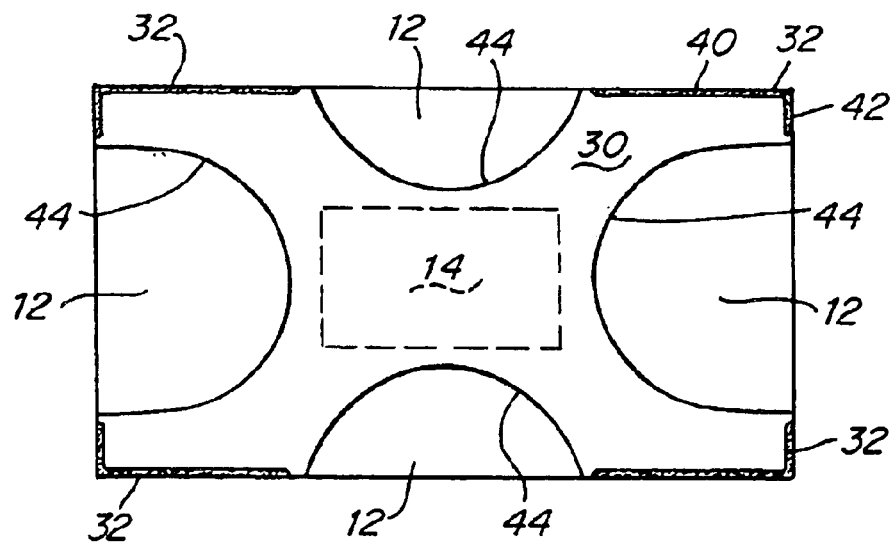
FIG. 7 is a top plan view of yet another further embodiment of the bandage of this invention.

In the embodiment of FIG. 7, layer 30 is affixed to substrate 12 at connections 32 which are located at each corner of substrate 12, and extend from the corners at least part of the way along adjacent edges 40 and 42 toward adjacent corners to provide a relatively large length for connection 32 to reduce the likelihood that layer 30 would be torn or separated from substrate 12 at connections 32.

Affixation may be produced such as through heat welding, by the use of adhesives, or in other known ways. In another embodiment, layer 30 and substrate 12 are integrally formed such as by molding. In another embodiment, layer 30 and substrate 12 are formed as a molded or extruded tube which is folded in half to form substrate 12 and layer 30 and to provide locations 32 which are disposed along a fold or crease, or a partial fold or crease.

In another aspect, as shown in FIGS. 1 and 2, substrate 12 includes an extension 26 that projects beyond the edge 18 of adhesive layer 16 and that is flexible. Layer 30 is affixed to substrate 12 at connections 32 on extension 26 that are disposed beyond edge 18 toward the outer edge or perimeter of substrate 12. As a result, as lateral forces are applied to layer 30 and layer 30 slides laterally or parallel to substrate 12, substrate 12 is permitted to flex in the vicinity of extensions 26 to facilitate greater lateral movement of layer 30 with respect to substrate 12. Typically, extensions 26 extend around the entire perimeter of substrate 12 and surround layer 14, as shown in FIG. 2, although extensions 26 could project beyond edge 18 on two opposite sides of protective layer 14, as shown in FIG. 3. In one embodiment of an oval-shaped structure, as shown in FIG. 4, an extension 26 is provided all around the perimeter of the substrate 12. In another embodiment of an oval-shaped layer 30, as shown in FIG. 5, extensions 26 are provided at selected locations on the corners of rectangular substrate 12.

Extensions 26 are not necessary to the invention. For example, in FIGS. 6 and 7, adhesive layer 16 covers all of surface 24 of substrate 12 beyond protective layer 14, and extends to the edges of substrate 12 all around the perimeter thereof.

The shape and size of structure 10 is not important, so long as protective layer 14 is able to completely cover a blister or wound, or an area to be protected. A typical shape is square, or rectangular, as illustrated in FIG. 2. However, other shapes, such as oval, as illustrated in FIG. 4, are also acceptable.

In another aspect of the invention, as illustrated in FIGS. 2 and 7, cutouts 44 may be provided in layer 30 between connections 32. Cutouts 44 may be used, for example, as shown in FIGS. 2 and 4, in conjunction with an extension 26, or as shown in FIG. 7, where there are no extensions 26, and adhesive layer 16 extends to the edge of substrate 12, so that edge 18 is coextensive with the outer perimeter of substrate 12. Cutouts 44 may be provided in square or rectangular shaped layers 30, as shown in FIGS. 2 and 7, or in round or oval layers 30, as shown in FIG. 4. Cutouts 44 may facilitate movement of layer 30 with respect to substrate 12 to permit a greater range of lateral movement. When used together, extensions 26 and cutouts 44 typically allow a greater range of lateral movement for layer 30 with respect to substrate 12 than would be possible without one or the other. However, cutouts 44 are not necessary to this invention.

Cutouts 44 may have a relatively large radius of curvature, as shown in FIG. 2. Alternatively, cutouts 44 could have a much shorter radius of curvature as shown in FIG. 7, and extend a substantial distance toward the center of layer 30. In FIG. 2, cutouts 44 only extend a very short distance toward the center of layer 30, thereby providing a greater area for surface 31 against which frictional forces may act, thereby reducing or minimizing the likelihood that any such frictional forces would act directly on substrate 12. In the embodiment of FIG. 7, a greater portion of the area of surface 31 is removed, thus allowing more frictional forces to act on substrate 12.

In another aspect of the invention, the structure 10 may be used to protect a wound or blister or to protect an area of the skin to prevent chaffing, formation of blisters or wounds caused by friction. In the method of this invention, release liner 28 is first removed by grasping flap 29 and separating release liner 28 from adhesive layer 16. Once adhesive layer 16 is exposed, it is applied to the skin such that the area of skin having a blister or wound that needs protection, or that must be protected from frictional or other forces to prevent chaffing, or the formation of wounds or blisters, is completely covered by layer 14. Adhesive layer 16 is then adhered to the surface of the skin surrounding the blister, wound or area to be protected, but preferably not touching the blister, wound, or area to be protected.

If the area of skin to be protected or the blister or wound is disposed on the foot, structure 10 is positioned so that layer 30 is disposed between the substrate covering the area to be protected and a sock or shoe placed on the foot. Any frictional forces resulting from movement of the sock or shoe with respect to the foot are applied to layer 30. Any component of these frictional forces in the plane of layer 30, causes movement of layer 30 generally parallel to surfaces 31 and 22 thereof, as shown by arrow 50 in FIG. 1. Since at least surface 22 and surface 20 are formed of a low-friction material, layer 30 slides easily with respect to substrate 12. Such movement is facilitated by cutouts 44 and extensions 26. Extensions 26 allow substrate 12 to flex, permitting a greater range of movement for layer 30. As a result, only a very small percentage of the frictional forces applied to layer 30 are transmitted to substrate 12. In addition, little or no heat is generated by the movement of layer 30 with respect to substrate 12. As a consequence, little or no movement of substrate 12 in the direction of arrow 50 with respect to the underlying skin is produced, protecting the skin from the frictional forces applied to layer 30.

A similar situation exists with respect to areas to be protected on other portions of the body. Typically, these other portions are covered by articles of clothing, and movement of the articles of clothing with respect to the body could cause lateral movement of layer 30 in the direction of arrow 50 with respect to substrate 12. Again, since movement of layer 30 is permitted with respect to substrate 12, little or no frictional forces are transmitted to substrate 12 resulting in little or no movement of substrate 12 with respect to the underlying area to be protected. In addition, as discussed above little or no frictional heat is generated.

For applications for the foot, the configuration illustrated in FIGS. 1 and 2 might be preferred, since layer 30 has a relatively large surface area, and since it permits a greater range of movement of layer 30 with respect to substrate 12, because of the provision of both cutouts 44 and extensions 26. In other applications, where a large range of movement is not expected or required, or where frictional forces are small, embodiments such as those shown in FIG. 5 or FIG. 6 might be preferred, since the lack of an extension 26 and cutouts 44 provides greater coverage of substrate 12 by layer 30, and therefore further reduces the likelihood that frictional forces are transmitted directly to surface 20 of substrate 12 by shoes or clothing and thus to the skin surface. The drawback is that the absence of cutouts 44 and the attachment of layer 30 to substrate 12 around the entire perimeter of substrate 12 may somewhat restrict the permissible range of movement of layer 30 with respect to substrate 12.

Protective layer 14 may also include medications such as antibiotics which could be used to promote healing. A layer of a lubricant such as Vaseline® or the like could also be applied to layer 14 to further minimize any frictional effects on the skin resulting from the application of frictional forces to structure 10, since such a lubricant would permit movement of protective layer 14 with respect to the underlying skin, blister or wound.

The present invention provides a relatively low-cost structure which is ideally suited for preventing chaffing or the formation of wounds or blisters, as well as for protecting blisters and wounds that are already formed from frictional forces that could cause them further damage. The relatively easy to use structure permits ready and easy application of the product to a portion of the body by the user. As indicated, this invention may be used with cuts or open wounds as well as blisters where it is desired to protect the cut or open wound or blister from frictional forces which could interfere with proper healing.

This invention is not limited in its application to the details of construction and the arrangement of components set forth in the above description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

Having thus described several aspects of at least one embodiment of this invention, it is to be appreciated that various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. An adhesive bandage for protection of areas on the skin, the bandage comprising:

a substrate having a perimeter, a first surface and a second surface on an opposite side of the first surface, the second surface of the substrate having a low coefficient of friction;

a protective layer disposed on the first surface of the substrate;

a layer of a pressure-sensitive adhesive disposed on the first surface of the substrate and surrounding at least a portion of the protective layer; and a sheet of material that is attached to the substrate at attachment locations adjacent the perimeter of the substrate, the sheet of material having a lower surface having a low coefficient of friction, the lower surface of the sheet confronting the second surface of the substrate and being constructed and located to move with respect to the second surface of the substrate in a direction generally parallel to the substrate.

2. The bandage as recited in claim 1, wherein the substrate is generally rectangular in shape, and wherein the sheet of material is attached to the substrate only at corners of the substrate.

3. The bandage as recited in claim 1, wherein the sheet of material includes cutouts disposed between the attachment locations.

4. The bandage as recited in claim 1, wherein the layer of adhesive extends to points spaced from the perimeter of the substrate at selected edges to provide extensions of the substrate adjacent the perimeter of the substrate which are free of adhesive.

5. The bandage as recited in claim 4, wherein the extensions are disposed around the entire perimeter of the substrate.

6. The bandage as recited in claim 4, wherein the extensions are disposed on opposite sides of the protective layer.

7. The bandage as recited in claim 4, wherein the extensions are flexible, thereby allowing a greater range of movement of the sheet of material with respect to the substrate.

8. The bandage as recited in claim 1, wherein the attachment locations are substantially continuous adjacent the entire perimeter of the substrate.

9. The bandage as recited in claim 1, wherein the attachment locations are spaced from one another.

10. The bandage as recited in claim 1, wherein the second surface of the substrate and the lower surface of the sheet of material both have a static coefficient of friction of about 1.0 or less.

11. The bandage as recited in claim 10, wherein the static coefficient of friction is about 0.7 or less.

12. The bandage as recited in claim 11, wherein the static coefficient of friction is in the range of about 0.2 to about 0.7.

13. The bandage as recited in claim 1, wherein the static coefficient of friction of the second surface of the substrate and the lower surface of the sheet of material is less than the static coefficient of friction of the area of skin being protected.

14. A bandage for the skin comprising:
a first layer having an outer perimeter, a first, low-friction surface, and a second surface;
an adhesive layer disposed on the second surface of the first layer, the adhesive layer extending to an adhesive edge which is spaced inwardly of the outer perimeter of the first layer at selected locations;
a second layer of low-friction material disposed adjacent the first surface of the first layer and being attached to the first layer at selected locations spaced from the adhesive edge toward the outer perimeter of the first layer.

15. The bandage as recited in claim 14, wherein the first and second layers are generally rectangular in shape, and wherein the second layer is attached to the first layer substantially at corners thereof.

16. The bandage as recited in claim 15, wherein the second layer of material includes cutouts between the corners of the first layer.

17. The bandage as recited in claim 14, wherein the second layer of material is affixed around its entire peripheral edge to the first layer.

18. The bandage as recited in claim 14, further comprising a protective layer which is substantially centrally disposed on the second surface of the first layer, and which is substantially surrounded by the layer of adhesive.

19. The bandage as recited in claim 14, wherein said first layer is heat-welded to the second layer.

20. The bandage as recited in claim 14, wherein the second layer and the first layer are integrally formed as a single sheet, and wherein the selected locations of attachment are formed as a crease in the single sheet.

21. A method for treating a blister comprising:
placing a bandage over a blister such that the blister is covered by a protective layer disposed on one side of the bandage;
adhesively securing the bandage to the skin using a layer of pressure-sensitive adhesive on the one side of the bandage that surrounds but does not touch the blister; and
affixing a sheet of low-friction material adjacent another side of the bandage, the sheet of low-friction material being constructed to be positioned between the bandage and items of clothing, the sheet of low-friction material being movable with respect to the bandage to minimize the transfer of any friction forces from items of clothing to the blister.

22. A method for protecting an area of the skin from chaffing or from the formation of blisters, the method comprising:
placing a protective layer of a bandage against the area of skin that is to be protected;
adhesively securing the bandage to the skin using a layer of pressure-sensitive adhesive that surrounds but does not touch the area of skin to be protected;
placing a low-friction surface on a side of the bandage opposite the protective layer; and
adhering a layer of low-friction material to the bandage between the low-friction surface on the bandage and items of clothing, the layer of low-friction material being movable with respect to the low-friction surface on the bandage to minimize the transfer of any frictional forces from clothing to the area of skin to be protected.

23. A bandage for the skin comprising:
a first layer formed of a low-friction material, the first layer having an upper surface and a lower surface;
a protective layer disposed on the lower surface of the first layer;
a layer of adhesive surrounding the protective layer on the lower surface of the first layer; and
a second layer of a low-friction material being disposed adjacent and attached to the upper surface of the first layer in such a manner that the second layer moves with respect to the upper surface of the first layer in a direction generally parallel to the upper surface of the first layer in response to forces applied to the second layer.

24. The bandage as recited in claim 23, wherein the second layer is only attached to the upper surface of the first layer at selected locations.

25. The bandage as recited in claim 24, wherein the second layer is attached at corners of the first layer.

26. The bandage as recited in claim 23, wherein the adhesive layer on the lower surface of the first layer extends to an adhesive edge that is spaced from an outer edge of the first layer.

27. The bandage as recited in claim 26, wherein the second layer is attached to the first layer only at locations spaced from the adhesive edge toward the outer edge of the first layer.

* * * * *